United States Patent [19]
Hall

[11] 4,379,739
[45] Apr. 12, 1983

[54] ELECTROLYTIC REDUCTION OF CEPHALOSPORIN P-NITROBENZYL ESTERS

[75] Inventor: David A. Hall, Indianapolis, Ind.

[73] Assignee: Eli Lilly and Company, Indianapolis, Ind.

[21] Appl. No.: 259,316

[22] Filed: Apr. 30, 1981

Related U.S. Application Data

[63] Continuation-in-part of Ser. No. 135,829, Mar. 31, 1980, abandoned.

[51] Int. Cl.³ .............................................. C25B 3/00
[52] U.S. Cl. ................................... 204/72; 204/59 R
[58] Field of Search ...................... 204/59 R, 72, 73 R

[56] References Cited

U.S. PATENT DOCUMENTS 3,632,850 1/1972 Garbrecht ............................. 544/18
3,792,995 2/1974 Ochiai et al. ........................... 204/72
4,042,472 8/1977 Hall .................................. 204/73 R

OTHER PUBLICATIONS

Mairanovsky, Angev. Chem. Int. Ed. Engl., vol. 15, No. 5, pp. 281–292 (1976).
Otaka et al., Chem. Abs., vol. 85, Abs. 160124b (1976).
Cephalosporins and Penicillins by Flynn, pub. by Acedemic Press (1972), pp. 147–151.

Primary Examiner—F. Edmundson
Attorney, Agent, or Firm—Joseph A. Jones; Arthur R. Whale

[57] ABSTRACT

Deesterification of cephalosporin p-nitrobenzyl esters by electrolytic reduction.

25 Claims, 1 Drawing Figure

ELECTROLYTIC REDUCTION OF CEPHALOSPORIN P-NITROBENZYL ESTERS

CROSS-REFERENCE

This application is a continuation-in-part of my copending application Ser. No. 135,829, filed Mar. 31, 1980, now abandoned.

BACKGROUND OF THE INVENTION

1. Field of the Invention

This invention provides a superior method for the removal of the p-nitrobenzyl (pNB) ester group from cephalosporin carboxylic acids. The process is economically important, because cephalosporin antibiotics are often processed in the form of pNB esters, since the esters are convenient and economical to handle in chemical processing. The ester group must eventually be removed, however, because the cephalosporins are used as pharmaceuticals in the acid or salt form.

The pNB ester group has been used in the manufacture of cephalosporins for some time. See U.S. Pat. No. 3,632,850, of Garbrecht. The pNB group has been removed chemically, such as with zinc and a strong acid, or catalytically, as taught by Garbrecht. Other deesterification methods have since been devised, such as the methods of Hatfield, using zinc and an α-hydroxycarboxylic acid, U.S. Pat. No. 4,091,214, or zinc and an organothiol, Belgian Pat. No. 856,288, and the method of Jackson, U.S. Pat. No. 3,799,924, using a dithionite salt.

All of the chemical and catalytic methods of deesterification, however, have the disadvantage that they may affect functional groups of the molecule other than the pNB ester. Indeed, the art suggests that reductive deesterification of cephalosporins having certain 3-substituent groups would reduce and cleave the 3-group, as well as the ester group. U.S. Pat. Nos. 3,792,995, of Ochiai, 4,008,228, of Chauvette, and 4,042,472, of Hall, show the reductive cleavage of such 3-groups to form 3-methyl or 3-exomethylene compounds. Hall and Ochiai show that electrolytic reduction can have that effect. Chauvette and Ochiai show such reductive cleavage without affecting ester groups, and Chauvette teaches that the pNB ester group will be unaffected while such a reductive cleavage is carried out.

2. State of the Art

The electrochemical art is well-developed, and the literature contains many examples of electrolytic reductions, some of which deal with the removal of protecting groups by electrolytic processes. Among such articles may be mentioned those by Mairanovsky, *Angew. Chem. Int. Ed. Engl.* 15 (5), 281–92 (1976), which describes in general terms the removal of carboxy-protecting groups, including the pNB group, from some carboxylic acids. Another pertinent article is that by Semmelhack and Heinsohn, *J. Am. Chem. Soc.* 94, 5139–40 (1972), which concerns the electrolytic removal of haloethoxy ester groups from carboxylic acids.

SUMMARY OF THE INVENTION

The present invention provides a selective process for electrolytically removing pNB ester groups from cephalosporin compounds. More particularly, the invention provides a process for preparing a compound of the formula

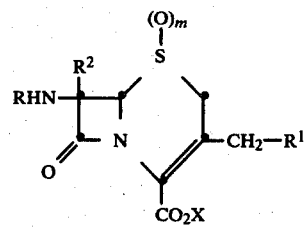

wherein
X is hydrogen;
m is 0 or 1;
$R^2$ is hydrogen or methoxy;
R is hydrogen or —$COR^3$;
$R^3$ is hydrogen, $C_1$-$C_3$ alkyl, halomethyl, benzyloxy, 2,2,2-trichloroethoxy, t-butoxy, $R^4$, $R^4$—(O)$_n$—$CH_2$—, $R^4$—$CH(R^5)$—, $R^6$—$CH_2$—, or

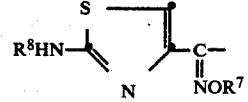

wherein $R^7$ is hydrogen or $C_1$-$C_3$ alkyl and $R^8$ is hydrogen or an amino-protecting group;
$R^4$ is cyclohexadienyl or phenyl, or cyclohexadienyl or phenyl substituted with one or two halo, hydroxy, protected hydroxy, aminomethyl, protected aminomethyl, $C_1$-$C_4$ alkyl or $C_1$-$C_4$ alkoxy groups;
n is 0 or 1;
$R^5$ is hydroxy, protected hydroxy, amino, protected amino, carboxy or protected carboxy;
$R^6$ is 2-thienyl, 2-furyl, 5-tetrazolyl or 1-tetrazolyl;
$R^1$ is $C_1$-$C_4$ alkanoyloxy, benzoyloxy, fluoro, chloro, carbamoyloxy, $C_1$-$C_4$ alkylcarbamoyloxy, pyridinio, pyridinio substituted with $C_1$-$C_4$ alkyl, $C_1$-$C_4$ alkanoyl, carbamoyl, $C_1$-$C_4$ alkylcarbamoyl, chloro, fluoro, hydroxy or trifluoromethyl, or the corresponding pyridinio chlorides or bromides, or —S—$R^9$;
$R^9$ is —$CH_2CO_2$($C_1$-$C_4$ alkyl), carbamoyl, phenyl, phenyl substituted with one or two chloro, fluoro, $C_1$-$C_4$ alkyl, hydroxy, $C_1$-$C_4$ alkylsulfonamido or trifluoromethyl groups; triazol-3-yl unsubstituted or substituted with one or two groups independently selected from $C_1$-$C_3$ alkyl, —$CO_2$($C_1$-$C_4$ alkyl), —$CONH_2$ and —$CH_2NHOCO$— (benzyl or $C_1$-$C_4$ alkyl);

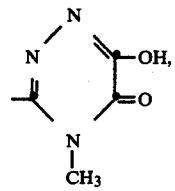

tetrazol-1-yl or tetrazol-5-yl substituted with one or two groups independently selected from $C_1$-$C_4$ alkyl and —$CH_2CO_2$($C_1$-$C_4$ alkyl or hydrogen); 4-cyano-5-aminopyrimidin-2-yl, or 5-methyl-1,3,4-thiadiazol-2-yl;
provided that n is 0 when $R^4$ is cyclohexadienyl;

which process comprises electrolytically reducing a compound of the above formula wherein X is p-nitrobenzyl in an acidic liquid medium comprising from about 0 to about 50% water, an acid having a $pK_a$ determined in water of 0 or below, the amount of said acid being at least four moles per mole of the compound to be reduced, and an organic solvent substantially inert to electrolytic reduction, at the working electrode of an electrolytic cell, said working electrode substantially comprising carbon, mercury, tin, aluminum, silver, copper, lead, chromium, zinc, nickel or cadmium, at a temperature from about 0° C. to about 75° C., at a potential in a range from about the potential of the initial onset of current flow of the first reduction to about the potential of the initial onset of current flow of the second reduction.

Figure 1:
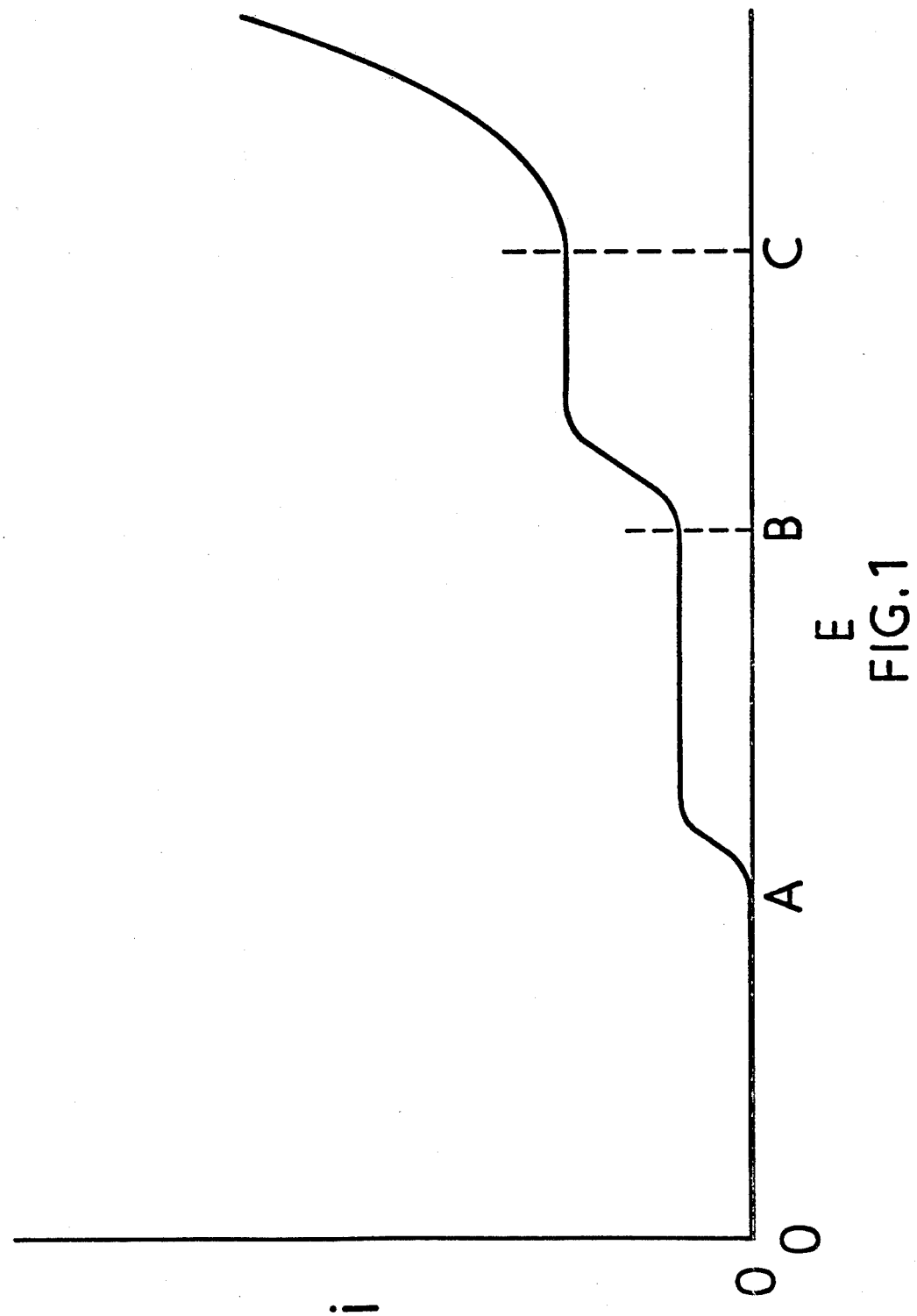
FIG. 1 is included to illustrate a typical voltammogram which results when a system adapted to the practice of this invention is subjected to an increasingly negative potential. The bottom axis, labeled E, measures the potential applied to the working electrode of the cell, compared to the reference electrode, and the potential is increasingly negative as one progresses to the right along the E axis.

The vertical axis, labeled i, indicates current flow through the cell, from the secondary electrode to the working electrode, and increases as one proceeds up the i axis.

A typical voltammogram curve is shown in FIG. 1. The curve is drawn in the usual manner, by slowly subjecting the system to increasingly negative potential, measuring the current at each potential, and plotting current against potential. The voltammogram shown represents a compound which has two groups subject to electrolytic reduction.

The first reduction occurs at the point of the E-i curve between A and B. Point A marks the initial onset of current flow of the first reduction, and point B marks the initial onset of current flow of the second reduction.

Point C indicates the onset of background discharge, which is the point where the solvent-electrolyte system begins to break down in an uncontrolled electrolysis, discharging hydrogen.

DESCRIPTION OF THE PREFERRED EMBODIMENTS

The compounds which are prepared by the process of this invention are known in the cephalosporin art. No new compounds are provided by the present invention. To assure that the reader understands the compounds, and understands the esters which are the starting compounds used in the present invention, some discussion and explanation of the formulae will be given.

In the above general formula, various generalized terms are used to describe the various groups. The generalized terms have their usual meanings in organic chemistry. For example, the term halomethyl includes bromomethyl, chloromethyl, fluoromethyl and iodomethyl.

The group $R^3$ is a 2-amino-4-thiazolyl(alkoxyimino)methyl group. The alkoxyimino group of this group may be in either the syn or anti form.

The terms $C_1$–$C_3$ alkyl, $C_1$–$C_4$ alkyl and $C_1$–$C_4$ alkoxy include groups such as methyl, ethyl, propyl, butyl, s-butyl, t-butyl, methoxy, isopropoxy and i-butoxy.

The term protected amino refers to an amino group substituted with one of the commonly employed amino-protecting groups such as t-butoxycarbonyl, benzyloxycarbonyl, 4-methoxybenzyloxycarbonyl, 2,2,2-trichloroethoxycarbonyl and 1-carbomethoxy-2-propenyl. Other accepted amino-protecting groups such as are described by J. W. Barton in *Protective Groups in Organic Chemistry*, J. F. W. McOmie, Editor, Plenum Press, New York, 1973, chapter 2 will be recognized by organic chemists as suitable for the purpose.

The term protected carboxy refers to an acid group protected with any group which is conventionally used to block or protect the carboxylic acid functionality of a cephalosporin while reactions involving other functional sites are carried out. Such carboxylic acid protecting groups are noted for their ease of cleavage and for their ability to protect the acid from unwanted reactions. Such groups are thoroughly described by E. Haslam in *Protective Groups in Organic Chemistry*, Chapter 5. Any such group may be used, of course. The preferred groups, however, are $C_1$–$C_4$ alkyl, $C_4$–$C_6$ t-alkyl, $C_5$–$C_8$ t-alkenyl, benzyl, methoxybenzyl, diphenylmethyl, phthalimidomethyl, succinimidomethyl or trichloroethyl.

Similarly, the term protected hydroxy refers to groups formed with a hydroxy group such as formyloxy, 2-chloroacetoxy, benzyloxy, diphenylmethoxy, triphenylmethoxy, phenoxycarbonyloxy, t-butoxy and methoxymethoxy. Other accepted hydroxy-protecting groups, such as those described by C. B. Reese in chapter 3 of *Protective Groups in Organic Chemistry* will be understood to be included in the term protected hydroxy.

Since the process of this invention is carried out in an acid medium, any acid-labile groups which may be on the starting compound will be attacked. Such groups include, for example, the widely used trimethylsilyl protecting group. Acid-labile groups should be avoided in the practice of this invention, unless it is desired to remove them from the starting compound.

The term $C_1$–$C_4$ alkanoyloxy includes groups such as formyloxy, acetoxy, propionyloxy and butyryloxy. The term $C_1$–$C_4$ alkylcarbamoyloxy includes N-methylcarbamoyloxy, N-propylcarbamoyloxy, N-i-butylcarbamoyloxy and the like groups.

The pyridinio and substituted pyridinio groups, and the pyridinio chlorides and bromides, are groups comprising a pyridine ring joined through its nitrogen, and having three double bonds, so that the nitrogen atom is in the quarternary form.

The term $C_1$–$C_4$ alkylsulfonamido refers to groups such as methylsulfonamido, ethylsulfonamido, isopropylsulfonamido and t-butylsulfonamido.

The following exemplary compounds which may be prepared by the process of this invention are mentioned to assure that the reader fully understands the use of the invention.

7-amino-7-methoxy-3-methoxycarbonylmethylthiomethyl-3-cephem-4-carboxylic acid 7-formamido-3-(3-fluorophenylthiomethyl)-4-carboxylic acid 7-acetamido-7-methoxy-3-(4-carbamoyl-1,2,4-triazol-3-ylthiomethyl)-3-cephem-4-carboxylic acid, 1-oxide 7-chloroacetamido-3-(3-propylsulfamoylphenylthiomethyl)-3-cephem-4-carboxylic acid 7-benzyloxyformamido-3-acetoxymethyl-3-cephem-4-carboxylic acid 7-amino-7-methoxy-3-(tetrazol-1-ylthiomethyl)-3-cephem-4-carboxylic acid 7-(2,2,2-trichloroethoxyformamido)-3-benzoyloxymethyl-3-cephem-4-carboxylic acid, 1-oxide 7-t-butoxyformamido-3-fluoromethyl-3-cephem-4-carboxylic acid 7-(1,4-cyclohexadienylformamido)-7-methoxy-3-chloromethyl-3-cephem-4-carboxylic acid 7-phenylformamido-7-methoxy-3-carbamoyloxymethyl-3-cephem-4-carboxylic acid 7-(4-chlorophenylformamido)-3-(N-methylcarbamoyloxymethyl)-3-cephem-4-carboxylic acid 7-(3-bromophenylformamido)-3-(N-butylcarbamoylthiomethyl)-3-cephem-4-carboxylic acid, 1-oxide 7-(2-fluorophenylformamido)-3-(tetrazol-5-ylthiomethyl)-3-cephem-4-carboxylic acid 7-(4-hydroxyphenylformamido)-3-(4-cyano-5-aminopyrimidin-2-ylthiomethyl)-3-cephem-4-carboxylic acid 7-(3-chloroacetoxyphenylformamido)-7-methoxy-3-pyridiniomethyl-3-cephem-4-carboxylic acid, chloride 7-(3-benzyloxyphenylformamido)-3-(4-methylpyridiniomethyl)-3-cephem-4-carboxylic acid 7-(4-benzyloxyphenylformamido)-3-(3-s-butylpyridiniomethyl)-3-cephem-4-carboxylic acid, bromide 7-(3,4-dihydroxyphenylformamido)-3-(4-formylpyridiniomethyl)-3-cephem-4-carboxylic acid 7-(2,4-dichlorophenylformamido)-7-methoxy-3-(2-butyrylpyridiniomethyl)-3-cephem-4-carboxylic acid, chloride, 1-oxide 7-(4-aminomethylphenylformamido)-3-(4-carbamoylpyridiniomethyl)-3-cephem-4-carboxylic acid, bromide 7-(3-t-butoxyformamidophenylformamido)-3-[3-(N-methylcarbamoyl)pyridiniomethyl]-3-cephem-4-carboxylic acid, chloride 7-(3-benzyloxyformamidophenylformamido)-3-[3-(N-propylcarbamoyl)pyridiniomethyl]-3-cephem-4-carboxylic acid, bromide 7-(2-propylphenylformamido)-3-(2-chloropyridiniomethyl)-3-cephem-4-carboxylic acid, chloride 7-(3,5-diethylphenylformamido)-3-(4-fluoropyridiniomethyl)-3-cephem-4-carboxylic acid, chloride 7-(4-methoxyphenylformamido)-7-methoxy-3-(4-hydroxypyridiniomethyl)-3-cephem-4-carboxylic acid 7-(2,5-dimethylphenylformamido)-3-(4-trifluoromethylpyridiniomethyl)-3-cephem-4-carboxylic acid, bromide 7-(3-s-butylphenylformamido)-3-(5-methyltetrazol-1-ylthiomethyl)-3-cephem-4-carboxylic acid 7-(3-butoxyphenylformamido)-3-fluoromethyl-3-cephem-4-carboxylic acid, 1-oxide 7-phenoxyacetamido-3-methoxycarbonylmethylthiomethyl-3-cephem-4-carboxylic acid 7-(1,3-cyclohexadienylacetamido)-3-isopropoxycarbonylmethylthiomethyl-3-cephem-4-carboxylic acid 7-(1,4-cyclohexadienylacetamido)-3-carbamoylthiomethyl-3-cephem-4-carboxylic acid 7-(4-hydroxy-1,4-cyclohexadienylacetamido)-7-methoxy-3-phenylthiomethyl-3-cephem-4-carboxylic acid 7-(2,4-dihydroxy-1,4-cyclohexadienylacetamido)-3-(2,4-dichlorophenylthiomethyl)-3-cephem-4-carboxylic acid 7-(3-chlorophenoxyacetamido)-3-(3-fluorophenylthiomethyl)-3-cephem-4-carboxylic acid 7-(2,4-difluorophenylacetamido)-3-(3-chloro-5-methylphenylthiomethyl)-3-cephem-4-carboxylic acid, 1-oxide 7-(4-triphenylmethoxy-1,4-cyclohexadienylacetamido)-3-(4-t-butylphenylthiomethyl)-3-cephem-4-carboxylic acid 7-(3-diphenylmethoxyphenoxyacetamido)-3-(2,4-dihydroxyphenylthiomethyl)-3-cephem-4-carboxylic acid 7-[3,5-di(aminomethyl)phenylacetamido]-3-[4-(N-i-butylsulfamoyl)phenylthiomethyl]-3-cephem-4-carboxylic acid 7-[4-(3-methoxybenzyloxyformamido)-phenylacetamido]-3-(4-trifluoromethylphenylthiomethyl)-3-cephem-4-carboxylic acid 7-(4-i-butylphenoxyacetamido)-3-(4-methyl-1,2,4-triazol-3-ylthiomethyl)-3-cephem-4-carboxylic acid 7-(3,5-dimethyl-1,4-cyclohexadienylacetamido)-3-(4-propyl-1,2,4-triazol-3-ylthiomethyl)-3-cephem-4-carboxylic acid, 1-oxide 7-(3-propoxy-1,3-cyclohexadienylacetamido)-3-(5-isopropyl-4-methoxycarbonyl-1,2,4-triazol-3-ylthiomethyl)-3-cephem-4-carboxylic acid 7-[2-(4-hydroxyphenyl)-2-hydroxyacetamido]-3-(4-butoxycarbonyl-1,2,4-triazol-3-ylthiomethyl)-3-cephem-4-carboxylic acid 7-[2-(1,4-cyclohexadienyl)-2-aminoacetamido]-3-[5-(N-methylcarbamoyl)-1,2,4-triazol-3-ylthiomethyl]-3-cephem-4-carboxylic acid 7-[2-(2,4-dichloro-1,3-cyclohexadienyl)-2-benzyloxyacetamido]-7-methoxy-3-(4-benzylcarbonyloxyaminomethyl-1,2,4-triazol-3-ylthiomethyl)-3-cephem-4-carboxylic acid, 1-oxide 7-[2-(3-diphenylmethoxyphenyl)-2-(t-butoxycarbonylamino)acetamido]-3-(4-acetoxyaminomethyl-1,2,4-triazol-3-ylthiomethyl)-3-cephem-4-carboxylic acid 7-[2-(2-chloro-5-methylphenyl)-2-carboxyacetamido]-3-(5-valeryloxyaminomethyl-1,2,4-triazol-3-ylthiomethyl)-3-cephem-4-carboxylic acid 7-(2-diphenylmethoxy-2-phenylacetamido)-3-(4-methyl-5-oxo-6-hydroxy-1,2,4-triazin-3-ylthiomethyl)-3-cephem-4-carboxylic acid 7-[2-(4-chloroacetoxyaminophenyl)-2-chloroacetoxyaminoacetamido]-7-methoxy-3-(tetrazol-1-ylthiomethyl)-3-cephem-4-carboxylic acid 7-[2-(1,4-cyclohexadienyl)-2-phenoxycarbonyloxyacetamido]-3-(tetrazol-5-ylthiomethyl)-3-cephem-4-carboxylic acid, 1-oxide 7-[2-(3-propyl-1,4-cyclohexadienyl)-2-(4-methoxybenzyloxycarbonyl)acetamido]-3-(4-methyltetrazol-5-ylthiomethyl)-3-cephem-4-carboxylic acid 7-[2-(2-hydroxy-1,4-cyclohexadienyl)-2-(2,2,2-trichloroethoxycarbonyl)acetamido]-7-methoxy-3-(5-butyltetrazol-1-ylthiomethyl)-3-cephem-4-carboxylic acid 7-[2-(1,3-cyclohexadienyl)-2-hydroxyacetamido]-3-(5-carboxymethyltetrazol-1-ylthiomethyl)-3-cephem-4-carboxylic acid 7-(2-thienylacetyl)-3-(2-methoxycarbonylmethyltetrazol-5-ylthiomethyl)-3-cephem-4-carboxylic acid 7-(2-furylacetamido)-3-(1-propoxycarbonylmethyltetrazol-5-ylthiomethyl)-3-cephem-4-carboxylic acid 7-(tetrazol-5-ylacetamido)-7-methoxy-3-phenylthiomethyl-3-cephem-4-carboxylic acid, 1-oxide 7-(tetrazol-1-ylacetamido)-3-phenylthiomethyl-3-cephem-4-carboxylic acid 7-[2-(2-amino-4-thiazolyl)-2-methoxyiminoacetamido]-3-acetoxymethyl-3-cephem-4-carboxylic acid 7-[2-(2-t-butoxycarbonylamino-4-thiazolyl)-2-ethox-
yiminoacetamido]-3-(5-methyl-1,3,4-thiadiazol-2-
ylthiomethyl)-3-cephem-4-carboxylic acid 7-[2-(2-[2,2,2-trichloroethoxycarbonylamino]-4-
thiazolyl]-2-propoxyiminoacetamido]-3-carbamoyl-
thiomethyl-3-cephem-4-carboxylic acid 7-[2-(2-benzyloxycarbonylamino-4-thiazolyl)-2-
methoxyiminoacetamido]-3-(2,4-dichlorophenylthi-
omethyl)-3-cephem-4-carboxylic acid 7-[2-(2-amino-4-thiazolyl)-2-isopropox-
yiminoacetamido]-3-acetoxymethyl-3-cephem-4-car-
boxylic acid All of the compounds of the formula above are known in the literature of the cephalosporin art, although the pNB esters of some of the compounds may not necessarily have been specifically described. Formation of esters of cephalosporin acids is a routine expedient in the art, however, as taught by U.S. Pat. No. 3,632,850. The pNB esters are usually formed at a relatively early stage in the synthesis of the cephalosporin, and the compound is carried through synthetic steps in the pNB ester form. The ester may be formed, for example, by simple contact of a cephalosporin acid with p-nitrobenzyl bromide in any convenient solvent at ambient temperature. It may also be advantageous to form the pNB ester of a penicillin, especially a penicillin 1-oxide, and transform the penicillin into a cephalosporin by one of the well-known ring expansion techniques. The cephalosporin ester so made may then be subjected to additional steps to form the desired compound, and finally deesterified by the process of this invention to obtain the antibiotically active cephalosporin acid.

Certain of the compounds described by the formula above are preferred for use in the process of this invention. Such preferred compounds are those of the following sub-generic types. It will be understood that preferred compounds may be obtained by combining various of the preferred sub-genera describing the groups.

(a) $R^2$ is hydrogen;
(b) $R^2$ is methoxy;
(c) R is hydrogen;
(d) R is $COR^3$;
(e) $R^3$ is hydrogen;
(f) $R^3$ is $R^4$—(O)$_n$—CH$_2$—;
  (1) $R^4$ is phenyl and n is 1;
  (2) $R^4$ is phenyl and n is 0;
  (3) $R^4$ is cyclohexadienyl;
  (4) $R^4$ is cyclohexadienyl or phenyl, substituted with 1 or 2 hydroxy or protected hydroxy groups;
(g) $R^3$ is $R^4$—CH($R^5$)—;
  (1) $R^4$ is phenyl and $R^5$ is amino or protected amino;
  (2) $R^4$ is cyclohexadienyl and $R^5$ is amino or protected amino;
  (3) $R^4$ is cyclohexadienyl or phenyl, substituted with 1 or 2 hydroxy or protected hydroxy groups, and $R^5$ is amino or protected amino;
  (4) $R^4$ is phenyl and $R^5$ is hydroxy or protected hydroxy;
  (5) $R^4$ is phenyl and $R^5$ is carboxy or protected carboxy;
(h) $R^3$ is 2-thienylmethyl;
(i) $R^3$ is

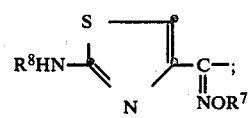

(1) $R^8$ is hydrogen;
(2) $R^8$ is an amino-protecting group;
(3) $R^7$ is methyl;
(j) $R^1$ is $C_1$–$C_4$ alkanoyloxy, carbamoyloxy or $C_1$–$C_4$ alkylcarbamoyloxy;
(k) $R^1$ is —S—$R^9$;
  (1) $R^9$ is a triazol-3-yl, tetrazol-1-yl, tetrazol-5-yl or thiadiazol-2-yl group as defined above;
  (2) $R^9$ is a triazol-3-yl group as defined above;
  (3) $R^9$ is a tetrazol-1-yl group as defined above;
  (4) $R^9$ is a thiadiazol-2-yl group as defined above;
  (5) $R^9$ is a tetrazol-5-yl group as defined above;
(l) m is 0.

A particularly preferred group of compounds includes those wherein $R^1$ is —S—$R^9$.

The most preferred products of the present process are 7-(tetrazol-1-ylacetamido)-3-(5-methyl-1,3,4-thiadiazol-2-ylthiomethyl)-3-cephem-4-carboxylic acid, and 7-(2-phenyl-2-hydroxyacetamido)-3-(1-methyltetrazol-5-ylthiomethyl)-3-cephem-4-carboxylic acid.

The electrolytic cells used for the process of this invention are the conventional types now known in the electrochemical art. This invention does not provide and does not need any new cells or other equipment. Some discussion of electrolytic cells will be given, however.

An electrolytic cell of the type used for electrolytic reductions has a working electrode, sometimes called the cathode, at which the reduction takes place. The working electrode is maintained at a potential which is negative with respect to the auxiliary electrode, or anode, at which only electrolyte reactions should take place. A reference electrode is usually used, also. The reference electrode, at which no reactions should take place, supplies a reference point from which the potential of the working electrode is measured. A typical and frequently-used reference electrode is the saturated calomel electrode; others are the mercury/mercuric chloride electrode and the silver/silver chloride electrode. The reference electrode is electrically connected to the working fluid through a conductive bridge or a porous junction.

Cells are very often divided into compartments, so that each of the electrodes is immersed in fluid which is physically separated from the fluids of the other compartments, but is electrically connected to them. Such division of the cell is optional in the context of the present invention, unless the compound to be reduced bears a group which can be electrically oxidized, such as the compounds in which R is 4-hydroxyphenylacetyl. In general, groups having oxygen substitution on an aromatic ring are likely to be readily oxidized. The oxidizability of the starting compound may be readily determined by running a voltammogram on the auxiliary electrode in a positive direction with respect to the reference electrode. The presence of inflection points, such as are shown in FIG. 1, indicates that one or more oxidizable groups are present and that a divided cell is necessary, so that the auxiliary electrode is physically separated from the working fluid which contains the compound.

The arrangement of electrolytic cells, the construction of electrodes, and the materials which may be effectively used as dividers are all part of the common knowledge of the electrochemical art, and may easily be learned by reference to text books and journal articles. Particularly useful text books which may be mentioned include Organic Electrochemistry, M. M. Baizer, Editor, Marcel Dekker, Inc., New York (1973), and Technique of Electroorganic Synthesis, N. L. Weinberg, Editor, John Wiley and Sons, New York (1974).

Working electrodes for use in the process of this invention are made of carbon, mercury, tin, aluminum, silver, copper, lead, chromium, zinc, nickel or cadmium. The preferred working electrodes are mercury, silver and lead. The electrodes should be rather highly purified, as is normally the case in electrochemistry. The form of the electrode is not important; it may be solid sheet, gauze or cloth, a basket of shot, or a fluidized bed of particles, with equally good results. The electrode may also be made of an inert substrate plated with the electrode metal, or it may be made in the form of a sheet of the electrode composition, wrapped with gauze of the same composition to increase the electrode area.

The auxiliary electrode does not participate in the reductive process, and so it may be made of any suitable substance which is not attacked by the oxidative side of the electrolytic process. Auxiliary electrodes are most often made of the noble metals, especially platinum, or of carbon. Platinum oxide, or platinum coated with platinum oxide, is the preferred anode composition. Lead oxide, silver oxide and such metallic oxides are also usable auxiliary electrode compositions.

It is most effective to arrange the cell so that the distance between the auxiliary electrode and the working electrode is everywhere the same, and is as small as possible. The relationship is desirable in all electrolytic processes, to maximize current flow and minimize temperature rise caused by the resistance of the fluid to the flow of current.

The process of this invention is carried out in an acidic working fluid, which is made acid by the addition of an acid having a $pK_a$ of 0 or less, determined in water, preferably sulfuric acid or hydrochloric acid. Other strong acids such as phosphoric acid, nitric acid, p-toluenesulfonic acid and the like may also be used.

The acid is necessary to give up protons to the reaction at the working electrode, and also to keep the working fluid acid, because the products are unstable in basic conditions. Since the reduction is a 4-electron process, the working fluid must contain at least four moles of acid per mole of compound to be reduced. Greater amounts of acid, even up to ten or twenty moles per mole of compound, may be used if desired.

If an undivided cell is used, the fluid in contact with both the working electrode and the auxiliary electrode will be the same. If the cell is divided, however, the working fluid will undoubtedly be different from the fluid in the auxiliary electrode compartment.

The working fluid used in this invention is a mixture containing up to about 50% water, preferably from about 10% to about 50% water. The organic portions of the working fluid may be either water-miscible or water-immiscible. It is preferred to use a water-miscible solvent, so that the working fluid is a homogeneous solution.

Suitable water-miscible organic solvents include the amides, especially dimethylformamide and dimethylacetamide, acetone, the water-miscible alkanols, such as methanol, ethanol and propanol, and tetrahydrofuran.

If a water-immiscible solvent is used in the working fluid, the choice of solvents is extremely broad, because any solvent may be used which is not reduced at the working electrode. Especially desirable solvents include the halogenated solvents, such as dichloromethane, 1,1,2-trichloroethane, chloroform, chlorobenzene, 1,1,1-trichloroethane and the like. Other immiscible solvents which may advantageously be used include the ketones including methyl ethyl ketone, methyl butyl ketone and methyl isobutyl ketone, to mention only those which are economically available in commerce, the aromatic solvents such as benzene, toluene and the xylenes, the alkanes such as pentane, hexane and the octanes, the alcohols such as phenol, the butyl alcohols and the like, and ethers such as diethyl ether, diisopropyl ether and hexahydropyran.

When a water-immiscible solvent is used, the working fluid necessarily consists of two distinct phases. The acid remains in the aqueous phase, of course, and it is necessary to provide an electrolyte for the solvent phase of the working fluid. Such electrolytes are commonly used in the electrochemical art, and are preferably chosen from the class of quaternary ammonium salts. Useful electrolytes for this purpose include, for example, tetraethylammonium perchlorate, tetrabutylammonium perchlorate, benzotributylammonium chloride, benzyltriethylammonium bromide, benzyltriethylammonium chloride, methyltributylammonium iodide, tribenzylethylammonium p-toluenesulfonate, and the like electrolytes.

The same organic electrolytes are used when the working fluid is non-aqueous, if the acid is immiscible with the solvent.

If the process of this invention is to be carried out in a divided cell, the divider may be made of any of the materials commonly used in electrochemistry for the purpose. Especially useful dividers are made from the ion exchange membranes, especially those which can pass cations. Dividers may also advantageously be made of finely porous substances such as ceramic membranes and sintered glass membranes. Such porous dividers may be made permeable to ions, but not to the fluids themselves, by sealing the membranes with a conductive gel, of which a typical example is agar gel saturated with an ionic substance such as, for example, potassium sulfate.

When the auxiliary electrode occupies a cell compartment by itself, it is immersed in a conductive fluid. If the divider is a porous membrane, it is advisable to provide an auxiliary electrode fluid which is compatible with the working fluid, such as an aqueous solution of the mineral acid used in the working fluid. If the cell divider is porous only to ions, then the auxiliary electrode fluid may be any convenient conductive fluid, such as dilute aqueous solutions of ionizable salts and acids.

The temperature of the process is from about 0° C. to about 75° C., preferably from about 0° C. to about 30° C.

The potential of the working electrode, or the potential between the working electrode and the auxiliary electrode, may be controlled in various ways. The most effective and precise way to control the potential is to use a reference electrode, with its junction to the working fluid placed as physically close as possible to the working electrode. The desired potential for the process is determined from examination of a voltammogram of the system, and the potential between the working electrode and the auxiliary electrode is adjusted to give the desired constant potential between the reference electrode and the working electrode. This method of control is much more effective than control by the overall voltage between the working electrode and the auxiliary electrode, because that voltage depends on the condition of the dividing membrane, if any, the concentration of the acid in the working fluid, and the concentration of the compound to be reduced in the working fluid.

Similarly it is relatively inefficient to control the system by means of the current flow between the auxiliary electrode and the working electrode, because the current flow is directly dependent on the concentration of the compound to be reduced, as well as upon the physical condition of the electrodes and of the divider. However, when an individual reduction has been thoroughly studied and the relationship between current, time and concentration is known, controlled-current electrolysis can be used for production of repeated batches.

Thus, the best way to control the system is by the potential between a reference electrode and the working electrode, and the control most advantageously is provided by an automatic instrument which constantly senses that potential and adjusts the voltage between the working electrode and auxiliary electrode accordingly. Such instruments are now readily available; one maker of them is Princeton Applied Research, Inc., Princeton, N.J., U.S.A.

As has been briefly discussed above, the potential for operating the process of this invention with any given combination of electrodes, working fluid and compound is determined according to the routine method of the electrochemical art, by running a voltammogram of the system. It has been found, in performing voltammograms of many compounds of the formula described above, that the first current plateau corresponds to the reduction of the nitro group of the p-nitrobenzyl group of these compounds. Accordingly, it is selectively possible to reduce that nitro group without affecting other portions of the compound. Once the nitro group has been reduced, the benzyl ester group spontaneously hydrolyzes from the compound, producing the antibiotic cephalosporin acid.

It is not possible, of course, to name a precise potential range for the operation of the process of this invention, since the potential for every system will necessarily be different. It has been observed, however, that the potential of the working electrode for reductions according to this process is from about $-0.3$ volt to about $-1$ volt, relative to a saturated calomel reference electrode, in the majority of systems which have been used.

The reduction of this invention appears to be a 4-electron process, and so the reduction of a grammole of compound requires 385,948 coulombs. The length of time necessary to pass this amount of current necessarily depends upon the overall resistance of the cell and the effective area of the electrodes.

Electrolytic cells usually require good agitation, and the process of this invention is typical in this respect. It has been found advisable to provide enough agitation of the working fluid to keep the surface of the electrode thoroughly swept, so that a fresh supply of compound to be reduced is constantly supplied to the working electrode. Further, when a water-immiscible solvent is used in the working fluid, it is necessary to agitate the fluid sufficiently well to keep the two phases of the working fluid intimately mixed in the form of fine droplets.

The electrochemical art has long known that electrolytic processes are carried out more advantageously in flow cells than in batch electrolytic cells, in general. A flow cell is an electrolytic cell arranged for the constant passage of the working fluid through the cell. The cell volume may be quite small, and the current density rather high, to achieve the desired extent of reaction in a single pass through the cell, or the flow rate may be lower and the volume higher, with the expectation that a number of passes through the cell will be necessary. In either event, the flow cell is operated continuously with no interruptions for filling and emptying the cell, and the associated operations of product isolation and temperature control are carried on outside the cell.

Flow cells are set up just as are batch cells, except for the necessary provisions for entry and exit of the working fluid. A flow cell may be divided, if necessary, in the usual manner. It is often possible to design a flow cell with the electrodes spaced advantageously close to each other, because the agitation of the working fluid is provided by its own flow velocity and it is unnecessary to provide for mechanical agitation of the cell. For example, a flow cell is often built in the form of a plate-and-frame filter press, with the electrodes in sheet form, clamped between the frames.

The concentration of the compound to be reduced in the working fluid is widely variable and is limited only by the solubility of the compound. Of course, it is most economical to use relatively high concentrations, in order to obtain the maximum effect from the solvents used in the process. However, workup of the fluid and isolation of the product from it is frequently more difficult when highly concentrated working fluids are used. Accordingly, it has not been advantageous in practice to use concentrations of compound in the working fluid higher than about 20% weight/volume.

The cephalosporin acid is recovered from the working fluid by a conventional isolation procedure. Typically, the working fluid is diluted with a large amount of dilute mineral acid, such as 1-normal hydrochloric acid, and the dilute solution is extracted with ethyl acetate. In some cases, it is advantageous to back-extract the organic layer with additional dilute acid, to remove as much as possible of the organic portions of the working fluid. The organic layer is then evaporated under vacuum to obtain the product, which may be further purified, as by recrystallization, if desired.

In isolating the product, it is separated from an impurity which is believed to be composed of polymers of the aminobenzyl moiety removed in the reduction. This polymeric impurity is formed in deesterifications according to the prior art methods, as well. The use of dimethylformamide as the solvent in the working fluid makes the isolation problem much easier, and back-extraction of the first organic layer obtained in the isolation steps, with dilute aqueous acid, is very useful in removing the polymeric impurity.

The following examples are included to assist the reader in understanding the process of this invention, and to assure that a skilled electrochemist can carry out any desired process of this invention. The products of the examples were identified by instrumental analytical techniques, as will be explained in the individual examples. Some products were made repeatedly by different embodiments of the process of the invention, and in such cases, the products were often merely identified by thin-layer chromatography (TLC) or by nuclear magnetic resonance (NMR) analysis as identical to the original product, and were not otherwise isolated or identified.

Much of the data in the following examples has been tabulated, to condense the information, and the compounds made by the processes to be described will be identified by the following code. It will be understood, of course, that in all cases the starting compound was the corresponding p-nitrobenzyl ester.

1. 7-phenoxyacetamido-3-(1-methyltetrazol-5-ylthiomethyl)-3-cephem-4-carboxylic acid
2. 7-(2-thienylacetamido)-3-(1-methyltetrazol-5-ylthiomethyl)-3-cephem-4-carboxylic acid
3. 7-(2-butoxycarbonylamino-2-phenylacetamido)-7-methoxy-3-(1-methyltetrazol-5-ylthiomethyl)-3-cephem-4-carboxylic acid
4. 7-(2-hydroxy-2-phenylacetamido)-3-(1-methyltetrazol-5-ylthiomethyl)-3-cephem-4-carboxylic acid
5. 7-phenoxyacetamido-3-(5-methyl-1,3,4-thiadiazol-2-ylthiomethyl)-3-cephem-4-carboxylic acid
6. 7-(2-thienylacetamido)-3-(5-methyl-1,3,4-thiadiazol-2-ylthiomethyl)-3-cephem-4-carboxylic acid
7. 7-(tetrazol-1-ylacetamido)-3-(5-methyl-1,3,4-thiadiazol-2-ylthiomethyl)-3-cephem-4-carboxylic acid
8. 7-phenoxyacetamido-3-acetoxymethyl-3-cephem-4-carboxylic acid
9. 7-(2-thienylacetamido)-3-benzoyloxymethyl-3-cephem-4-carboxylic acid
10. 7-(2-thienylacetamido)-3-(4-carbamoylpyridiniomethyl)-3-cephem-4-carboxylic acid, bromide
11. 7-(2-thienylacetamido)-3-(4-chlorophenylthiomethyl)-3-cephem-4-carboxylic acid
12. 7-(2-thienylacetamido)-3-methoxycarbonylmethylthiomethyl-3-cephem-4-carboxylic acid
13. 7-(2-thienylacetamido)-3-t-butoxycarbonylmethyllthiomethyl-3-cephem-4-carboxylic acid
14. 7-(2-thienylacetamido)-7-methoxy-3-carbamoylthiomethyl-3-cephem-4-carboxylic acid
15. 7-(2-thienylacetamido)-3-fluoromethyl-3-cephem-4-carboxylic acid
16. 7-(2-thienylacetamido)-3-(1-carboxymethyltetrazol-5-ylthiomethyl)-3-cephem-4-carboxylic acid
17. 7-(2-thienylacetamido)-3-(5-amino-4-cyanopyrimidin-2-ylthiomethyl)-3-cephem-4-carboxylic acid
18. 7-[2-(2-triphenylmethylaminothiazol-4-yl)-2-methoxyiminoacetamido]-3-(6-hydroxy-4-methyl-5-oxo-1,2,4-triazin-3-ylthiomethyl)-3-cephem-4-carboxylic acid, 1-oxide
19. 7-(2-thienylacetamido)-3-(1H-pyrazolo[3,4-d]pyrimidin-4-ylthiomethyl)-3-cephem-4-carboxylic acid
20. 7-(2-thienylacetamido)-3-(1H-pyrazolo[4,3-d]pyrimidin-7-ylthiomethyl)-3-cephem-4-carboxylic acid
21. 7-(2-thienylacetamido)-3-(4-benzylcarbonyloxyaminomethyl-1,2,4-triazol-3-ylthiomethyl)-3-cephem-4-carboxylic acid
22. 7-(2-thienylacetamido)-3-(5-carbamoyl-4-methyl-1,2,4-triazol-3-ylthiomethyl)-3-cephem-4-carboxylic acid
23. 7-(2-t-butoxycarbonylamino-2-phenylacetamido)-3-(5-carbamoyl-4-methyl-1,2,4-triazol-3-ylthiomethyl)-3-cephem-4-carboxylic acid
24. 7-[2-(2-triphenylmethylaminothiazol-4-yl)-2-methoxyiminoacetamido]-3-(5-carbamoyl-4-methyl-1,2,4-triazol-3-ylthiomethyl)-3-cephem-4-carboxylic acid
25. 7-[2-(2-triphenylmethylaminothiazol-4-yl)-2-methoxyiminoacetamido]-3-(4-methyl-1,2,4-triazol-3-ylthiomethyl)-3-cephem-4-carboxylic acid
26. 7-(2-thienylacetamido)-3-(5-aminomethyl-1,2,4-triazol-3-ylthiomethyl)-3-cephem-4-carboxylic acid
27. 7-(2-thienylacetamido)-3-(5-ethoxycarbonyl-4-methyl-1,2,4-triazol-3-ylthiomethyl)-3-cephem-4-carboxylic acid The examples which follow are arranged in groups, according to the variations in the operating conditions under which they were run. Most of the operating data are tabulated.

The first group of examples were run in small batch electrolytic cells, having volumes from about 10 to 100 ml.

EXAMPLES 1–21

In these examples, the working fluid was comprised of 90% by volume of dimethylformamide, and 10% by volume of 12 N sulfuric acid. The working electrode was a toroidal mercury pool having an area, in various experiments, of from 14 to 20 cm.$^2$. The auxiliary electrode was a loop of platinum wire, parallel to the surface of the working electrode, and separated from the working electrode by a fine glass frit. The reference electrode, in all experiments, was a saturated calomel electrode, with its junction placed physically as close as possible to the surface of the working electrode. In some experiments, the cell was an H-type cell with the three electrodes in separate tubes, separated by fine glass frits. An automatic potentiostat was used to control the potential between the working electrode and the reference electrode, and in most cases no measurement of overall voltage of the cell was made. The current flows recorded in the table below indicate the approximate maximum current flow at the beginning of the experiment; the current flow, of course, declined steadily as the starting compound was used up.

Many experiments were run at controlled temperatures; room temperature experiments are indicated by R.T.

Operating conditions which were not recorded by the operator are indicated by N.R.

In the tables below, the total time of the experiment is indicated, to the nearest 10 minutes, and the total amount of current passed is expressed in terms of a percentage of the theoretical amount of current necessary to accomplish a 4-electron reaction.

The products were isolated by diluting the working fluid with a large amount of dilute aqueous acid, usually hydrochloric acid, and extracting the diluted solution several times with portions of ethyl acetate. The organic layers were then back-extracted several times with additional portions of dilute aqueous acid, and evaporated to dryness under vacuum to obtain the product. In general, the products were not further purified. Physical-chemical characterizing data for the products is tabulated after the tables showing the operating conditions of the experiments.

The working fluid in all of the experiments was kept free of air by bubbling argon slowly through it.

TABLE 1

| Example | Compound | G./ml. | Temp. | Potential | Max. Current | Time | Total Current | Product Yield |
|---|---|---|---|---|---|---|---|---|
| 1 | 1 | 4/40 | 25° C. | −0.4 v. | 400 ma | 470 min | 87% | 2.31 g. |
| 2 | 1 | 2/24 | 25° | −0.5 | 300 | 320 | 80% | 1.11 |
| 3 | 2 | 0.4/ | 25° | −0.4 | 400 | 180 | 61% | 0.16 |
| 4 | 3 | 9.9/100 | 25° | −0.4 | 400 | 90 | 86% | 3.85 |
| 5 | 4 | .25/15 | R.T. | −0.4 | 40 | 150 | 15% | 0.12 |
| 6 | 7 | .2/15 | R.T. | −0.5 | 30 | 220 | 100% | 0.09 |
| 7 | 8 | 4.9/60 | 25° | N.R. | 400 | 530 | 96% | 1.8 |
| 8 | 9 | 0.06/30 | 25° | −0.35 | 9 | 220 | 76% | N.R. |
| 9 | 13 | 0.84/35 | 25° | −0.38 | 130 | 220 | 102% | 0.575 |
| 10 | 14 | 0.08/30 | 25° | N.R. | N.R. | N.R. | N.R. | 0.035 |
| 11 | 15 | 0.04/10 | 22° | −0.4–0.6 | N.R. | N.R. | N.R. | N.R. |
| 12 | 16 | 0.68/30 | 25° | −0.4 | 160 | 180 | 102% | N.R. |
| 13 | 19 | 0.5/37 | 25° | −0.4 | 54 | 330 | 100% | 0.12 |
| 14 | 21 | 0.51/35 | 25° | −0.5 | 50 | 370 | N.R. | 0.094 |
| 15 | 22 | 0.2/10 | 21° | −0.5 | 40 | 210 | 80% | 0.04 |
| 16 | 23 | 0.36/25 | 25° | −0.4 | 60 | 330 | 93% | N.R. |
| 17 | 23 | 0.91/35 | 25° | −0.5 | 60 | 370 | 79% | 0.275 |
| 18 | 24 | 1.5/40 | 25° | −0.45 | N.R. | N.R. | N.R. | 0.15 |
| 19 | 24 | 1.5/40 | 25° | −0.475 | N.R. | N.R. | N.R. | 0.1 |
| 20 | 26 | 0.5/30 | 25° | −0.475 | 60 | 270 | 78% | N.R. |
| 21 | 27 | 0.2/10 | 21° | −0.4 | 30 | 220 | 107% | 0.1 |

The following NMR features were observed in analysis of the compounds prepared in the examples above.

Compound 1, 60 mHz instrument in DMSOd$_6$; δ 3.73 (broad s); 3.95 (s); 4.31 (broad s); 4.63 (s); 5.10 (d, J=4.5 Hz); 5.75 (dd, J=8 Hz and 4.5 Hz); 6.70–7.5 (m); 9.13 (d, J=8 Hz)

Compound 2, 100 mHz instrument in DMSOd$_6$; δ 3.70 (ABq), 3.77 (s); 3.93 (s) 4.31 (ABq); 5.08 (d, J=4.5 Hz); 5.67 (dd, J=8 Hz and 4.5 Hz); 6.85–7.42 (m); 9.12 (d, J=8 Hz)

Compound 3, 100 mHz instrument in DMSOd$_6$; δ 1.91 (s); 3.38 (s); 3.46 (ABq); 3.90 (s); 4.25 (ABq); 5.06 (s); 5.34 (d, J=8 Hz); 7.2–7.6 (m); 9.47 (broad s)

Compound 4, 60 mHz instrument in DMSOd$_6$; δ 3.68 (broad s); 3.93 (s); 4.30 (broad s); 5.06 (d, J=4.5 Hz); 5.11 (broad s); 5.71 (dd, J=8 Hz and 4.5 Hz); 7.18–7.65 (m); 8.68 (d, J=8 Hz)

Compound 7, 60 mHz instrument in DMSOd$_6$; δ 2.17 (s); 3.69 (ABq); 4.38 (ABq); 5.12 (d, J=4.5 Hz); 5.37 (s); 5.72 (dd, J=8 Hz and 4.5 Hz); 9.36 (s); 9.50 (d, J=4.5 Hz)

Compound 8, 60 mHz instrument in DMSOd$_6$; δ 2.03 (s); 3.60 (broad s); 4.63 (s); 4.90 (ABq); 5.10 (d, J=4.5 Hz); 5.76 (dd, J=8 Hz); 6.7–7.5 (m); 9.08 (d)

Compound 9, 100 mHz instrument in acetone d$_6$; δ 3.77 (ABq); 3.90 (s); 5.19 (d, J=4.5 Hz); 5.26 (ABq); 5.85 (dd, J=8 Hz and 4.5 Hz); 6.85–8.15 (m); 8.05 (d, J=8 Hz)

Compound 13, 100 mHz instrument in DMSOd$_6$; δ 1.41 (s); 3.22 (ABq); 3.51 (ABq); 3.67 (broad s); 3.76 (s); 5.09 (d, J=4.5 Hz); 5.63 (dd, J=8 Hz and 4.5 Hz); 6.95 (m); 7.35 (m); 9.09 (d, J=8 Hz)

Compound 14, no analysis

Compound 15, 60 mHz instrument in acetone d$_6$; δ 3.71 (broad s); 3.98 (s); 5.36 (d, J=48 Hz); 5.25 (d, J=4.5 Hz); 5.78 (dd, J=8 Hz and 4.5 Hz); 6.9–7.5 (m); 8.16 (d, J=8 Hz)

Compound 16, 100 mHz instrument in DMSOd$_6$; δ 3.66 (ABq); 3.75 (s); 4.33 (ABq); 5.05 (d, J=4.5 Hz); 5.3 (s); 6.95 (m); 7.35 (m); 9.12 (d, J=8 Hz)

Compound 19, 60 mHz instrument in DMSOd$_6$; δ 3.53 (ABq); 3.78 (s); 4.53 (ABq); 5.13 (d, J=4.5 Hz); 5.71 (dd, J=8 Hz and 4.5 Hz); 6.85–7.40 (m); 8.15 (s); 8.90 (s); 9.16 (d, J=8 Hz);

Compound 21, 60 mHz instrument in DMSOd$_6$; δ 3.73 (broad s); 3.85 (s); 4.28 (ABq); 4.40 (d, J=6 Hz); 5.13 (d, J=4.5 Hz); 5.15 (s); 5.76 (dd, J=8 Hz and 4.5 Hz); 7.41 (s); 7.78 (t, J=6 Hz); 9.20 (J=8 Hz);

Compound 22, 60 mHz instrument in DMSOd$_6$; δ 3.68 (broad s); 3.78 (s); 3.77 (s); 4.19 (ABq); 5.07 (d, J=4.5 Hz); 5.66 (dd, J=8 Hz and 4.5 Hz); 6.85–7.40 (m); 7.83 (broad s); 8.17 (broad s); 9.14 (d=8 Hz)

Compound 23, 60 mHz instrument in DMSOd$_6$; δ 1.36 (s); 3.59 (broad s); 3.77 (s); 4.14 (broad s); 4.98 (d, J=4.5 Hz); 5.31 (d, J=9 Hz); 5.67 (dd, J=8 Hz and 4.5 Hz); 7.15–7.50 (m); 7.82 (broad s) 8.16 (broad s); 9.17 (d, J=8 Hz)

Compound 24, 360 mHz instrument in DMSOd$_6$; δ 3.64 (ABq); 3.77 (s); 3.81 (s); 4.18 (ABq); 5.09 (d, J=4.5 Hz); 5.68 (dd, J=8 Hz and 4.5 Hz); 6.71 (s); 7.2–7.4 (m); 7.86 (broad s); 8.21 (broad s); 8.84 (s); 9.58 (d, J=8 Hz)

Compound 26, no analysis

Compound 27, 60 mHz instrument in DMSO d$_6$; δ 1.33 (t, J=7 Hz); 3.68 (broad s); 3.78 (q, J=7 Hz); 4.23 (broad s); 4.39 (q, J=7 Hz); 5.07 (d, J=4.5 Hz); 5.66 (dd, J=8 Hz and 4.5 Hz); 6.85–7.40 (m); 9.14 (d, J=8 Hz)

EXAMPLES 22–29

The following examples report experiments run according to the method described above, except that, in these examples, the auxiliary electrode was separated from the working electrode by a frit coated with an electrically conductive gel. In some experiments, the gel was formed from agar made with an ionizable salt solution, and in other experiments, the frit was coated with methyl cellulose gel made conductive in the same manner.

TABLE 2

| Example | Compound | G./ml. | Temp. | Potential | Max. Current | Time | Total Current | Product Yield |
|---|---|---|---|---|---|---|---|---|
| 22 | 5 | 4.1/50 | R.T. | −0.5 | N.R. | 280 | 78% | 2.06 g. |
| 23 | 5 | 1.5/40 | R.T. | −0.5 | 130 | 120 | N.R. | 0.84 |

TABLE 2-continued

| Example | Compound | G./ml. | Temp. | Potential | Max. Current | Time | Total Current | Product Yield |
|---|---|---|---|---|---|---|---|---|
| 24 | 10 | 0.4/25 | 25° | N.R. | 30 | 230 | 77% | N.R. |
| 25 | 11 | 0.1/35 | 25° | −0.4 | 13 | 320 | 100% | 0.035 |
| 26 | 12 | 0.63/24 | 25° | −0.5−0.7 | 23 | 150 | 90% | N.R. |
| 27 | 17 | 0.8/30 | 25° | −0.4 | N.R. | N.R. | 91% | 0.38 |
| 28 | 20 | 1.62/25 | 25° | −0.45 | 200 | 330 | 97% | 0.27 |
| 29 | 6 | 1/25 | 25° | −0.4 | 150 | 330 | 92% | 0.6 |

Compound 5, 60 mHz instrument in DMSOd$_6$; δ 2.67 (s); 3.68 (ABq); 4.37 (ABq); 4.61 (s); 5.12 (d, J=4.5 Hz); 5.71 (dd, J=8 Hz and 4.5 Hz); 6.8–7.4 (m); 9.09 (d, J=8 Hz)

Compound 10 identified only by TLC

Compound 11, 60 mHz instrument in acetone d$_6$; δ 3.71 (ABq); 3.93 (s); 4.23 (ABq); 5.13 (d, J=4.5 Hz); 5.80 (dd, J=8 Hz and 4.5 Hz); 6.83–7.73 (m); 8.08 (d, J=8 Hz)

Compound 12, 100 mHz instrument in DMSOd$_6$; δ 3.34 (s); 3.61 (s); 3.67 (s); 3.76; 5.12 (d, J=4.5 Hz); 5.66 (dd, J=8 Hz and 4.5 Hz); 6.85–7.40 (m); 9.09 (d, J=8 Hz)

Compound 17, 60 mHz instrument in DMSOd$_6$; δ 3.68 (broad s); 3.78 (s); 4.20 (ABq); 5.13 (d, J=4.5 Hz); 5.66 (dd, J=8 Hz and 4.5 Hz); 6.95 (m); 7.35 (m); 7.93 (broad s); 8.40 (s)

Compound 20, 60 mHz instrument in DMSOd$_6$; δ 3.5 (broad s); 5.63 (dd, J=8 Hz and 4.5 Hz); 6.98 (m); 7.37 (m); 8.45 (s); 8.78 (s); 9.08 (d, J=8 Hz)

Compound 6, 60 mHz instrument in DMSOd$_6$; δ 2.63 (s); 3.70 (ABq); 3.80 (s); 4.41 (ABq); 5.14 (d, J=4.5 Hz); 5.73 (dd, J=8 Hz and 4.5 Hz); 6.90–7.50 (m); 9.16 (d, J=8 Hz)

EXAMPLES 30-31

The experiments reported in these examples were carried out in the same manner as the experiments of examples 1–21, except that the working and auxiliary electrodes were separated by an ion exchange membrane.

TABLE 3

| Example | Compound | G./ml. | Temp. | Potential | Max. Current | Time | Total Current | Product Yield |
|---|---|---|---|---|---|---|---|---|
| 30 | 18 | 0.4/37 | 25° C. | −0.34 v. | 20 ma | 150 min | 34% | 0.09 g. |
| 31 | 25 | 1/30 | 17° | −0.45 | 90 | 220 | 96% | 0.12 |

Compound 18, no analysis

Compound 25, 100 mHz instrument in CDCl$_3$; δ 3.65 (s); 3.70 (ABq); 4.0 (s); 4.25 (broad s); 5.12 (d, J=4.5 Hz); 5.82 (dd); 6.70 (s); 7.15–7.50 (m); 8.33 (s);

EXAMPLE 32

The experiment of this example was also carried out according to the methods described in the text of examples 1–21, except that the working and auxiliary electrodes in this experiment were not separated.

TABLE 4

| Example | Compound | G./ml. | Temp. | Potential | Max. Current | Time | Total Current | Product Yield |
|---|---|---|---|---|---|---|---|---|
| 32 | 1 | 0.6/50 | 25° C. | −0.4 v. | 500 ma | N.R. | N.R. | 0.15 g. |

EXAMPLE 33

The experiment of this example was also carried out according to the process as described in the text of examples 1–21, except that the working electrode was lead, rather than mercury.

TABLE 5

| Example | Compound | G./ml. | Temp. | Potential | Max. Current | Time | Total Current | Product Yield |
|---|---|---|---|---|---|---|---|---|
| 33 | 3 | 0.6/85 | 25° C. | −0.8 v. | 100 ma | 370 min | N.R. | N.R. |

EXAMPLE 34

The method described in the text of Examples 1–21 was used for this experiment also, except that the working fluid was made up of 90% dimethylformamide and 10% of 24 N sulfuric acid.

TABLE 6

| Example | Compound | G./ml. | Temp. | Potential | Max. Current | Time | Total Current | Product Yield |
|---|---|---|---|---|---|---|---|---|
| 34 | 3 | 11/100 | 25° C. | −0.4 v. | 350 ma. | N.R. | N.R. | 4 g. |

EXAMPLE 35

In the following example, the working fluid was a mixture of dimethylformamide and hydrochloric acid, as detailed in the table below. In other respects, the cell and method were as described in the text introducing Examples 1–21, except that the working and auxiliary electrodes were separated by a frit coated with a gel, as described in the introduction to Examples 22–29.

TABLE 7

| Cpd. | HCl | HCl Conc. | G./ml | Temp. | Potential | Max. Current | Time | Total Current | Product Yield |
|---|---|---|---|---|---|---|---|---|---|
| 5 | 10% | 2N | 0.5/80 | R.T. | −0.45 v. | N.R. | 370 min. | 84% | 0.24 g. |

EXAMPLE 36

The working fluid in this experiment was a mixture of 45% of tetrahydrofuran and 55% of an 0.1 M solution of pH 4.6 buffer. The measured pH of the working fluid, with the compound dissolved in it, was 5.5, and the pH of the working fluid was held at 5.5 throughout the experiment by the use of a pH controller which added 2 N sulfuric acid as necessary.

The working electrode was mercury, and the auxiliary electrode was a plantinum wire, separated from the working electrode by a fine glass frit coated with potassium sulfate-saturated agar. The reference electrode was saturated calomel, with the porous junction placed as close as possible to the working electrode.

TABLE 8

| Example | Compound | G./ml. | Temp. | Potential | Max. Current | Time | Total Current | Product Yield |
|---|---|---|---|---|---|---|---|---|
| 36 | 1 | 0.45/90 | 25° C. | −0.73 v. | 25 ma | 250 min | 57% | 0.17 |

I claim:
1. A process for preparing a compound of the formula

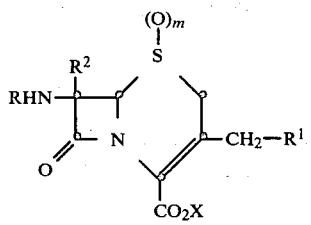

wherein
X is hydrogen;
m is 0 or 1;
$R^2$ is hydrogen or methoxy;
R is hydrogen or —$COR^3$;
$R^3$ is hydrogen, $C_1$—$C_3$ alkyl, halomethyl, benzyloxy, 2,2,2-trichloroethoxy, t-butoxy, $R^4$, $R^4$—(O)-$_n$—$CH_2$—, $R^4$—$CH(R^5)$—, $R^6$—$CH_2$—, or

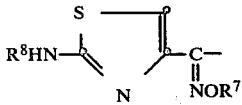

wherein $R^7$ is hydrogen or $C_1$-$C_3$ alkyl and $R^8$ is hydrogen or an amino-protecting group;
$R^4$ is cyclohexadienyl or phenyl, or cyclohexadienyl or phenyl substituted with one or two halo, hydroxy, protected hydroxy, aminomethyl, protected aminomethyl, $C_1$-$C_4$ alkyl or $C_1$-$C_4$ alkoxy groups;
n is 0 or 1;
$R^5$ is hydroxy, protected hydroxy, amino, protected amino, carboxy or protected carboxy;
$R^6$ is 2-thienyl, 2-furyl, 5-tetrazolyl or 1-tetrazolyl;
$R^1$ is $C_1$-$C_4$ alkanoyloxy, benzoyloxy, fluoro, chloro, carbamoyloxy, $C_1$-$C_4$ alkylcarbamoyloxy, pyridinio, pyridinio substituted with $C_1$-$C_4$ alkyl, $C_1$-$C_4$ alkanoyl, carbamoyl, $C_1$-$C_4$ alkylcarbamoyl, chloro, fluoro, hydroxy or trifluoromethyl, or the corresponding pyridinio chlorides or bromides, or —S—$R^9$;
$R^9$ is —$CH_2CO_2(C_1$-$C_4$ alkyl), carbamoyl, phenyl, phenyl substituted with one or two chloro, fluoro, $C_1$-$C_4$ alkyl, hydroxy, $C_1$-$C_4$ alkylsulfonamido or trifluoromethyl groups; triazol-3-yl unsubstituted or substituted with one or two groups independently selected from $C_1$-$C_3$ alkyl, —$CO_2(C_1$-$C_4$ alkyl), —$CONH_2$ and —$CH_2NHOCO$(benzyl or $C_1$-$C_4$ alkyl);

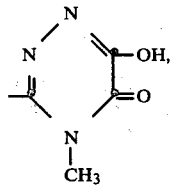

tetrazol-1-yl or tetrazol-5-yl substituted with one or two groups independently selected from $C_1$-$C_4$ alkyl and —$CH_2CO_2(C_1$-$C_4$ alkyl or hydrogen); 4-cyano-5-aminopyrimidin-2-yl, or 5-methyl-1,3,4-thiadiazol-2-yl;
provided that n is 0 when $R^4$ is cyclohexadienyl;
which process comprises electrolytically reducing a compound of the above formula wherein X is p-nitrobenzyl in an acidic liquid medium comprising from about 0 to about 50% water, an acid having a $pK_a$ determined in water of 0 or below, the amount of said acid being at least four moles per mole of the compound to be reduced, and an organic solvent substantially inert to electrolytic reduction, at the working electrode of an electrolytic cell, said working electrode substantially comprising carbon, mercury, tin, aluminum, silver, copper, lead, chromium, zinc, nickel or cadmium, at a temperature from about 0° C. to about 75° C., at a potential in a range from about the potential of the initial onset of current flow of the first reduction to about the potential of the initial onset of current flow of the second reduction.

2. A process of claim 1 wherein the acidic liquid medium comprises from about 10% to about 50% water.

3. A process of claim 1 wherein the organic solvent is water-miscible.

4. A process of claim 1 wherein the organic solvent is dimethylformamide.

5. A process of claim 1 wherein the organic solvent is tetrahydrofuran.

6. A process of claim 1 wherein the acid is hydrochloric acid.

7. A process of claim 1 wherein the acid is sulfuric acid.

8. A process of claim 1 wherein the cell is a divided cell.

9. A process of claim 1 wherein the working electrode comprises silver, lead or mercury.

10. A process of claim 1 wherein the potential is controlled by means of a reference electrode.

11. A process of claim 3 wherein the acidic liquid medium comprises from about 10% to about 50% water.

12. A process of claim 11 wherein the organic solvent is dimethylformamide or tetrahydrofuran.

13. A process of claim 12 wherein the acid is hydrochloric acid or sulfuric acid.

14. A process of claim 13 wherein the working electrode comprises silver, lead or mercury.

15. A process of claim 14 wherein the cell is a divided cell.

16. A process of claim 15 wherein the potential is controlled by means of a reference electrode.

17. A process of claim 3, 4 or 5 wherein the acid is hydrochloric acid or sulfuric acid.

18. A process of claim 17 wherein the acidic liquid medium comprises from about 10% to about 50% water.

19. A process of claim 2, 3, 4 or 5 wherein the cell is a divided cell.

20. A process of claim 19 wherein the working electrode comprises silver, lead or mercury.

21. A process of any one of claims 1–16 wherein the product is a compound wherein $R^1$ is $-S-R^9$.

22. A process of claim 21 wherein $R^9$ is a triazol-3-yl, tetrazol-1-yl, tetrazol-5-yl or thiadiazol-2-yl group.

23. A process of claim 22 wherein the product is a compound wherein R is $-COR^3$, and $R^3$ is a $R^4$, $R^4-(O)_n-CH_2-$, or $R^4-CH(R^5)-$ group.

24. A process of any one of claims 1–16 wherein the product is 7-(tetrazol-1-ylacetamido)-3-(5-methyl-1,3,4-thiadiazol-2-ylthiomethyl)-3-cephem-4-carboxylic acid.

25. A process of any one of claims 1–16 wherein the product is 7-(2-phenyl-2-hydroxyacetamido)-3-(1-methyltetrazol-5-ylthiomethyl)-3-cephem-4-carboxylic acid.

* * * * *